United States Patent
Oosaki et al.

(10) Patent No.: US 7,408,155 B2
(45) Date of Patent: Aug. 5, 2008

(54) MEASURING METHOD AND ITS APPARATUS

(75) Inventors: Mayuka Oosaki, Yokohama (JP); Hiroki Kawada, Tsuchiura (JP); Ryo Nakagaki, Kawasaki (JP); Chie Shishido, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 288 days.

(21) Appl. No.: 11/202,146

(22) Filed: Aug. 12, 2005

(65) Prior Publication Data

US 2006/0060774 A1 Mar. 23, 2006

(30) Foreign Application Priority Data

Sep. 22, 2004 (JP) .............................. 2004-274337

(51) Int. Cl.
G03F 7/20 (2006.01)
G03F 7/40 (2006.01)

(52) U.S. Cl. ..................... 250/310; 250/311; 250/307; 250/492.3

(58) Field of Classification Search .................. 367/53; 250/310, 311, 307, 492.3; 430/30, 22, 328
See application file for complete search history.

(56) References Cited

U.S. PATENT DOCUMENTS

| 6,583,413 | B1 * | 6/2003 | Shinada et al. | 250/310 |
| 7,053,371 | B2 * | 5/2006 | Ojima et al. | 250/310 |
| 7,091,485 | B2 * | 8/2006 | Kang et al. | 250/310 |
| 7,095,022 | B2 * | 8/2006 | Nakasuji et al. | 250/310 |
| 7,098,455 | B2 * | 8/2006 | Shinada et al. | 250/310 |
| 7,173,268 | B2 * | 2/2007 | Tanaka et al. | 250/559.19 |
| 2001/0006216 | A1 * | 7/2001 | Koike | 250/398 |
| 2001/0021546 | A1 * | 9/2001 | Suwa | 438/200 |
| 2005/0247876 | A1 * | 11/2005 | Kawada et al. | 250/310 |
| 2007/0023657 | A1 * | 2/2007 | Takane et al. | 250/310 |

FOREIGN PATENT DOCUMENTS

JP 11-316115 11/1999

OTHER PUBLICATIONS

J.S. Villarrubia et al., "A Simulation Study of Repeatability and Bias in the CD-SEM", Proceedings of SPIE vol. 5038 (2003), pp. 138-149.

* cited by examiner

*Primary Examiner*—Nikita Wells
*Assistant Examiner*—Johnnie L Smith
(74) *Attorney, Agent, or Firm*—Antonelli, Terry, Stout & Kraus, LLP.

(57) ABSTRACT

A method for measuring a dimension of a pattern formed on a sample using a secondary electron image obtained by picking up an image of the sample using a scanning electron microscope includes: obtaining a secondary electron image of a sample by picking up an image of the sample using a scanning electron microscope; creating, using the secondary electron image, an image profile of a pattern whose dimension is to be measured, within the obtained secondary electron image; retrieving a model profile that matches best with the created image profile from a plurality of model profiles pre-stored that are obtained from respective secondary electron images of a plurality of patterns, the cross sections of the plurality of patterns being of known shapes and dimensions and being different in shape; and obtaining a dimension of the pattern using information of the retrieved model profile.

10 Claims, 9 Drawing Sheets

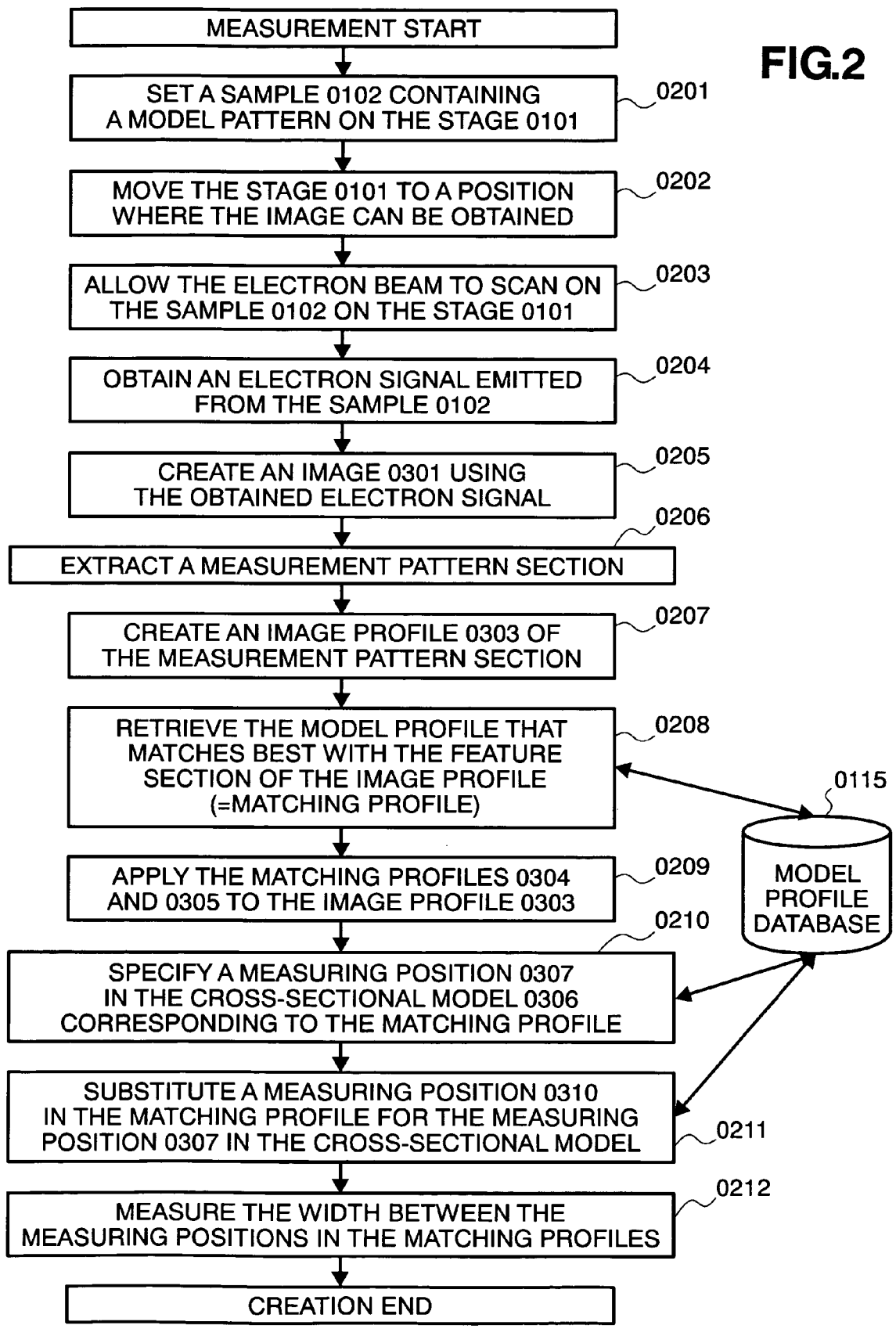

0301
0302 IMAGE SELECTION AREA

0306 CROSS-SECTIONAL MODEL
0307 SPECIFIED MEASURING POSITION

0304 LEFT MATCHING PROFILE
0305 RIGHT MATCHING PROFILE
0303 IMAGE PROFILE
0308 MATCHING PROFILE MEASURING POSITION
0309 LEFT MEASURING POSITION
0310 RIGHT MEASURING POSITION
0311 MEASUREMENT VALUE 0501
0502 IMAGE SELECTION AREA

0503 IMAGE PROFILE
0509 CENTER POSITION
0506 RIGHT FEATURE SECTION
0505 LEFT FEATURE SECTION

0506 MODEL PROFILE
0508 MEASURING POSITION: A
0508 MEASURING POSITION: B
0507 CROSS-SECTIONAL MODEL

0510 CONFORMED CROSS-SECTIONAL PROFILE

0504 CROSS-SECTIONAL PROFILE

FIG.6
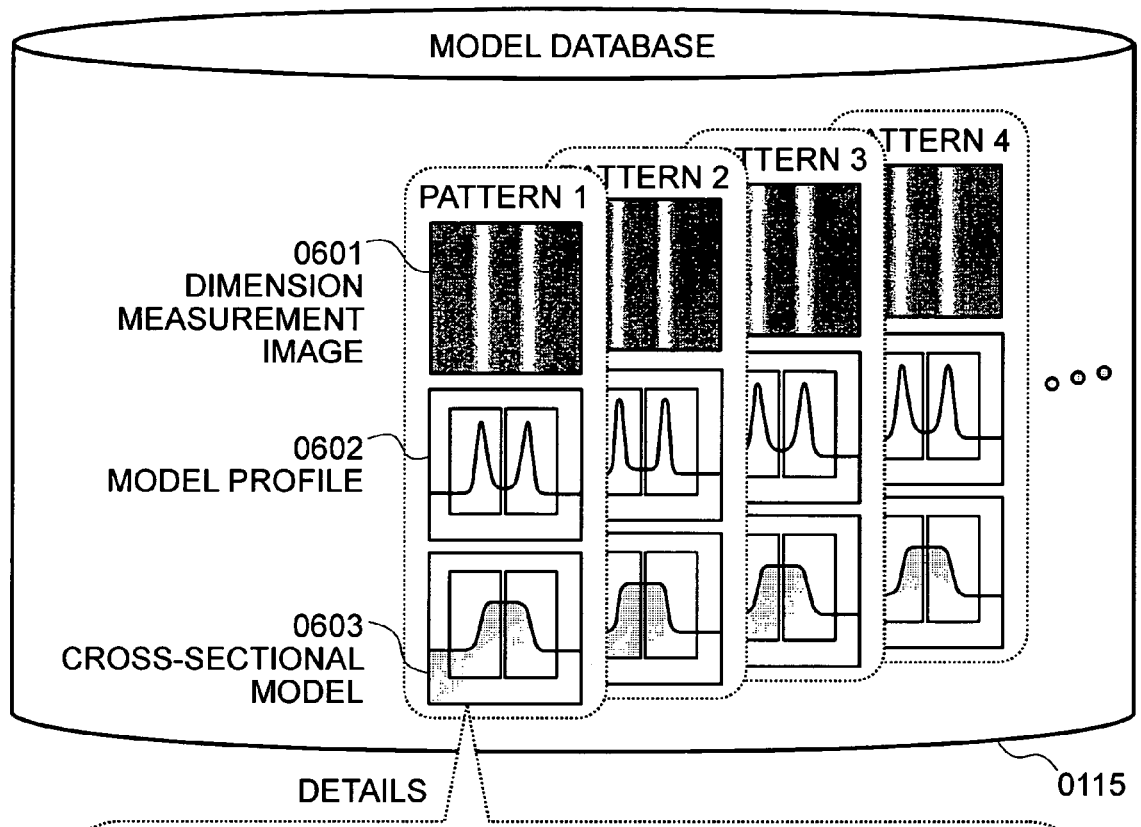
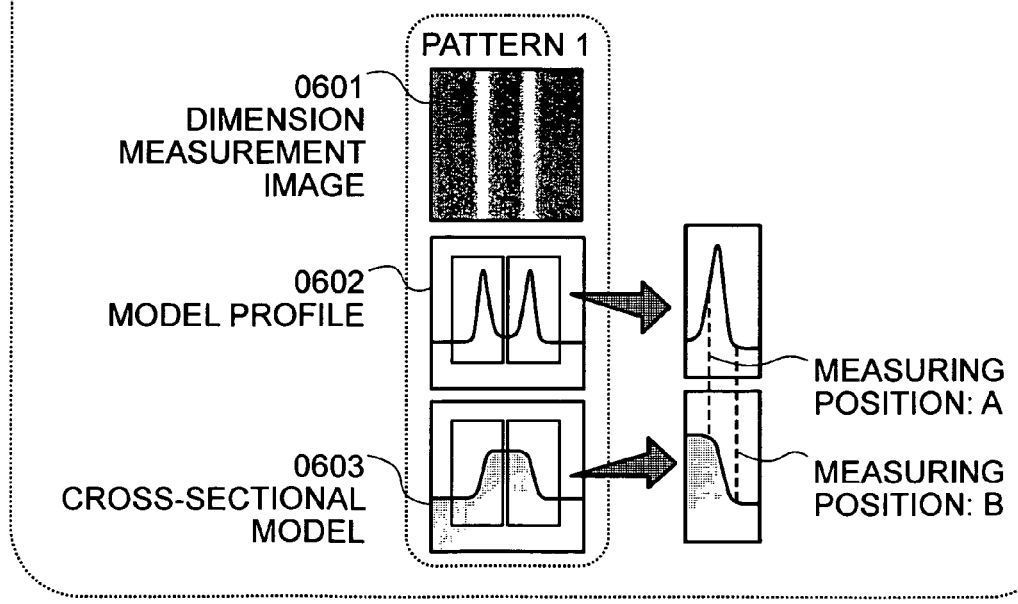

- 0303 IMAGE PROFILE
- 0802 MEASURING POSITION OF MODEL A
- MATCHING

- 0801 MODEL PROFILE
- HEIGHT 50%
- 0115
- MODEL A  MODEL B  MODEL C  MODEL D  MODEL E

- 0802 X-COORDINATE OF MEASURING POSITION
- 0804
- MODEL A
- MODEL B
- 0805
- 0806
- MODEL C
- 0807
- MODEL D
- MODEL E
- MATCHING RATE (LOW ⇔ HIGH)
- 0803

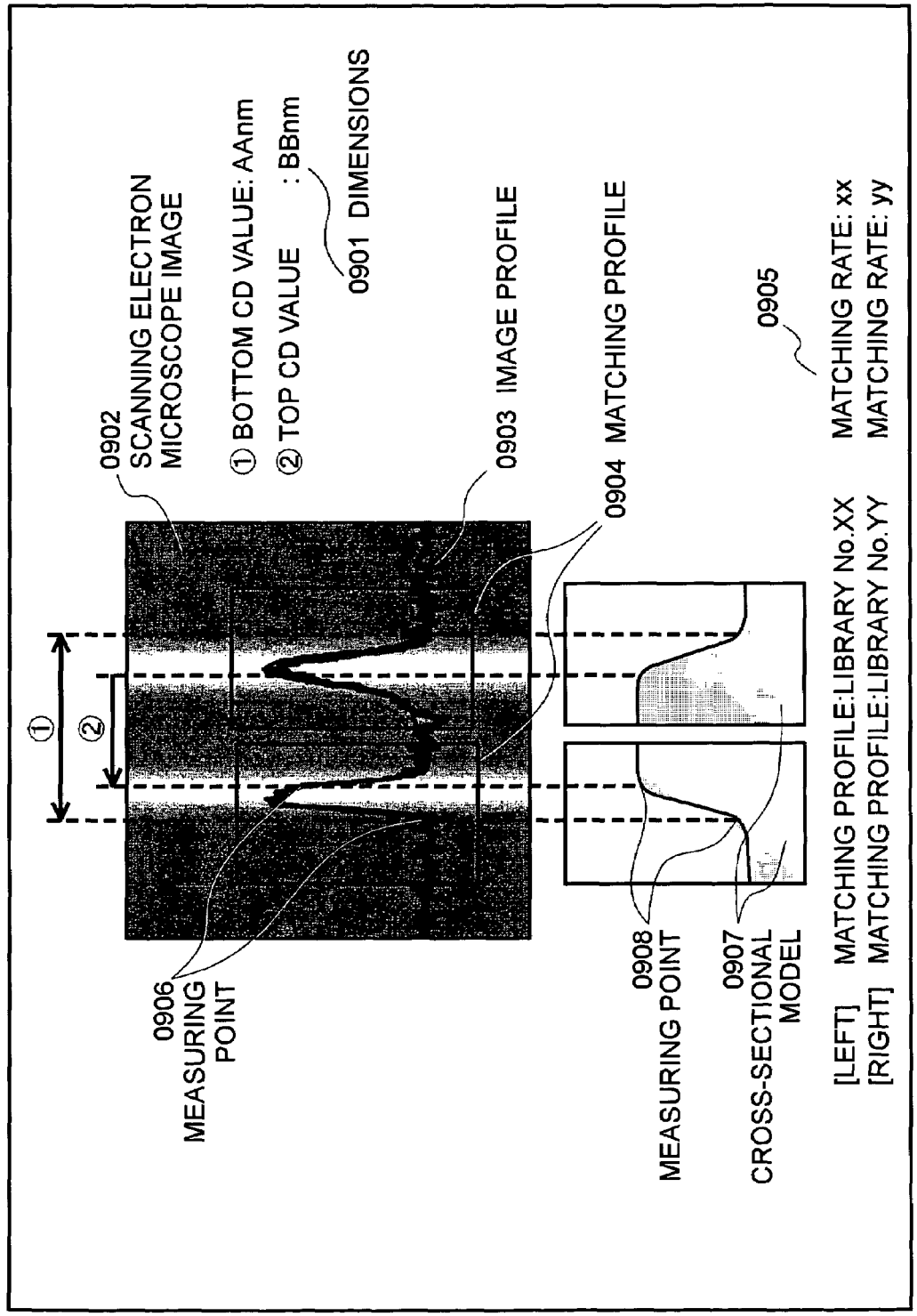

MEASURING METHOD AND ITS APPARATUS

BACKGROUND OF THE INVENTION

The present invention relates in general to an electron microscope of the types used for measuring a dimension of a fine pattern formed on a semiconductor substrate, and, more particularly, the invention relates to a scanning electron microscope having the function of calculating measurement data associated with a dimension measuring position in a cross section of a pattern.

In semiconductor wafer manufacturing processes, finer design of multilayer thin-film patterns formed on a wafer has been advancing rapidly, and process monitoring to monitor whether or not the patterns are formed as designed is becoming increasingly important. According to the 2002 edition of the ITRS (International Technology Roadmap for Semiconductors), which shows a roadmap for finer patterns of semiconductors, it is anticipated that the wiring pattern width of a transistor gate, where the finest pattern on a semiconductor wafer is formed, will become approximate 25 nm or less in about 2007. Therefore, it is necessary to have the ability to accurately measure such a fine pattern at a semiconductor manufacturing site from now on.

Scanning electron microscopes for use in pattern width measurement (measuring SEM (Scanning Electron Microscope), or a CD (Critical Dimension) SEM) that can pick up the image of a pattern under a hundred thousand to two hundred thousand magnifications, have conventionally been employed as a dimension measurement tool for measuring the width of a fine pattern in the order of several tens of nanometers. Patent Reference 1 (JP-A No. 11-316115) describes an example of dimension measurement processing employing such a scanning electron microscope. In this example, a pattern dimension is calculated as the distance between the left and right measuring points detected in an image profile created from a part area in the picked-up image of a pattern under measurement by averaging a signal wave of the pattern in the longitudinal direction of the pattern.

In addition to this, a method for measuring pattern dimensions by verifying the image profile of a pattern to be measured against a library of image profiles of various cross-sectional shapes that have been created beforehand with an electron beam simulation is disclosed in Non-Patent Reference 2 (A Simulation Study of Repeatability and Bias in the CD-SEM. J. S. Villarrubia et al., Metrology, Inspection, and Process Control for Microlithography XVII. pp. 138).

At the time of measuring a pattern of a semiconductor, which is likely to become increasingly finer, it can be considered that the measuring position in the cross-sectional shape of the pattern will become important from now on. For example, at the time of measuring the width of the wiring pattern of a transistor gate, since the bottom dimension of the wiring pattern of the gate largely affects characteristics of the transistor, it is necessary to accurately control the width of the bottom at the manufacturing site. Thus, from now on, it is necessary to perform manufacturing control using a dimension measurement value corresponding to a measuring position in the cross-sectional shape of the pattern.

However, in employing a dimension measurement method using conventional technology, a pattern dimension is calculated as the distance between the left and right measuring points detected in an image profile created from the picked-up image of the pattern under measurement. Methods for detecting pattern edges from the image profile include a method of specifying a height position on the image profile and a method of specifying a point of a specific slope on the image profile. However, in these methods, since a measuring position is determined from only the obtained image profile information, there is no clear correlation between a measuring position detected from the image profile and a measuring position in the cross-sectional shape of the pattern.

Methods for measuring a clear measuring point in the cross-sectional shape of a pattern currently include a method of observing a cross-section of a cut semiconductor wafer with a scanning electron microscope, etc., and a method of observing with an AFM (Atomic Force Microscope). However, there is a disadvantage have in that it is costly and time-consuming to perform these methods.

Further, in the method for measuring pattern dimensions by verifying the image profile of a pattern to be measured against a library of image profiles of various cross-sectional shapes that have been created beforehand with an electron beam simulation, as disclosed in non-patent document 1, the ability to obtain a dimension corresponding to the cross-sectional shape of the pattern has not been achieved at this time. Further, measuring dimensions with the method disclosed in non-patent document 1 is based on the assumption that models of various dimensions and shapes have been prepared in large quantities, whereas there is a problem in that dimension measurement cannot be performed with high accuracy in the case of a small number of models.

SUMMARY OF THE INVENTION

The present invention has been made in view of the foregoing considerations, and it is an object of this invention to provide a measuring method and its apparatus that can control a pattern bottom dimension which affects, for example, characteristics of a transistor as a result of enabling the measuring of a pattern dimension at a desired position on a cross-sectional shape of a pattern using an image profile obtained from a scanning electron microscope image of the pattern.

It is another object of this invention to provide a measuring method and its apparatus that brings about fewer models to be prepared beforehand by enabling accurate measurement with fewer models at the time of dimension measurement when applying a model that the apparatus stores beforehand to an image profile of the pattern to be measured.

According to one aspect of the invention, a method for measuring a dimension of a pattern formed on a sample using a secondary electron image obtained by picking up an image of the sample using a scanning electron microscope includes the steps of: obtaining a secondary electron image of a sample by picking up an image of the sample using a scanning electron microscope; creating an image profile of a pattern whose dimension is to be measured within the obtained secondary electron image using the secondary electron image; retrieving a model profile that matches best with the created image profile from a plurality of prestored model profiles that are obtained respectively from secondary electron images of a plurality of patterns, the cross sections of the plurality of patterns being of known shapes and dimensions and being different in shape; and obtaining a dimension of the pattern using information of the retrieved model profile.

According to another aspect of the invention, a method for measuring a dimension of a pattern formed on a sample using a secondary electron image obtained by picking up an image of the sample using a scanning electron microscope includes the steps of: creating an image profile of a pattern whose dimension is to be measured from a secondary electron image of a sample, the secondary electron image being obtained by picking up an image of the sample using a scanning electron microscope; obtaining a model profile that matches best with the image profile from a database that stores a plurality of model profiles that are obtained respectively from secondary electron images of cross sections of a plurality of patterns, the cross sections being of known dimensions and being different in shape; specifying a location for dimension measurement on a cross-sectional profile of the pattern whose cross-section corresponding to the obtained model profile is of a known dimension; obtaining a dimension of a desired location of the pattern from a location on the model profile, which corresponds to the location for dimension measurement specified on the cross-sectional profile; and displaying the obtained dimension of the desired location, the obtained model profile, the image profile, and the secondary electron image of the pattern, on the same screen.

According to yet another aspect of the invention, an apparatus for measuring a dimension of a pattern formed on a sample using a secondary electron image obtained by picking up an image of the sample using a scanning electron microscope includes: a scanning electron microscope device for obtaining a secondary electron image of a sample by irradiating an electron beam so as to be converged on the sample and allowing the electron beam to scan; an image profile creation device for creating an image profile of a pattern whose dimension is to be measured within the secondary electron image obtained by the scanning electron microscope device using the secondary electron image; a storage device for storing a plurality of model profiles that are obtained respectively from cross-sectional profiles of a plurality of patterns and secondary electron images of the plurality of patterns, the cross sections of the plurality of patterns being of known shapes and dimensions and being different in shape; a model profile retrieving device for retrieving a model profile that matches best with the image profile created by the image profile creation device from the plurality of model profiles stored in the storage device; and a dimension calculation device for obtaining a dimension of the pattern using the model profile retrieved by the model profile retrieving device.

According to various aspects of the invention, the scanning electron microscope is able to control a pattern bottom dimension which affects, for example, characteristics of a transistor as a result of enabling the measuring of a pattern dimension at a desired position on a cross-sectional shape of a pattern using an image profile obtained from a scanning electron microscope image of the pattern.

According to various aspects of the invention, it becomes possible to employ fewer models to be prepared beforehand because accurate measurement is enabled with fewer models at the time of dimension measurement when applying a model that the apparatus stores beforehand to an image profile of the pattern to be measured. Further, by thus performing dimension measurement when applying a model to an image profile of the pattern to be measured, it becomes possible to perform relatively accurate measurement on a low S/N image as well.

These and other objects, features and advantages of the invention will be apparent from the following more particular description of preferred embodiments of the invention, as illustrated in the accompanying drawings.

BRIEF DESCRIPTION OF THE DRAWINGS

In the drawings:

FIG. 2 is a flow diagram showing a pattern dimension measuring process according to an embodiment of the present invention;

FIG. 6 is a diagram of a database storing model files and cross-sectional models;

FIG. 9 is a diagram which shows an example of a display screen in which an image profile is overlaid on a SEM image, and, further, a cross-sectional model is displayed together.

DESCRIPTION OF THE PREFERRED EMBODIMENTS

Various embodiments of the present invention will be described below in detail with reference to the accompanying drawings.

Embodiment 1

The present invention aims to measure a dimension of a fine pattern using an image obtained by picking up an image of the fine pattern with a scanning electron microscope.

Figure 1:
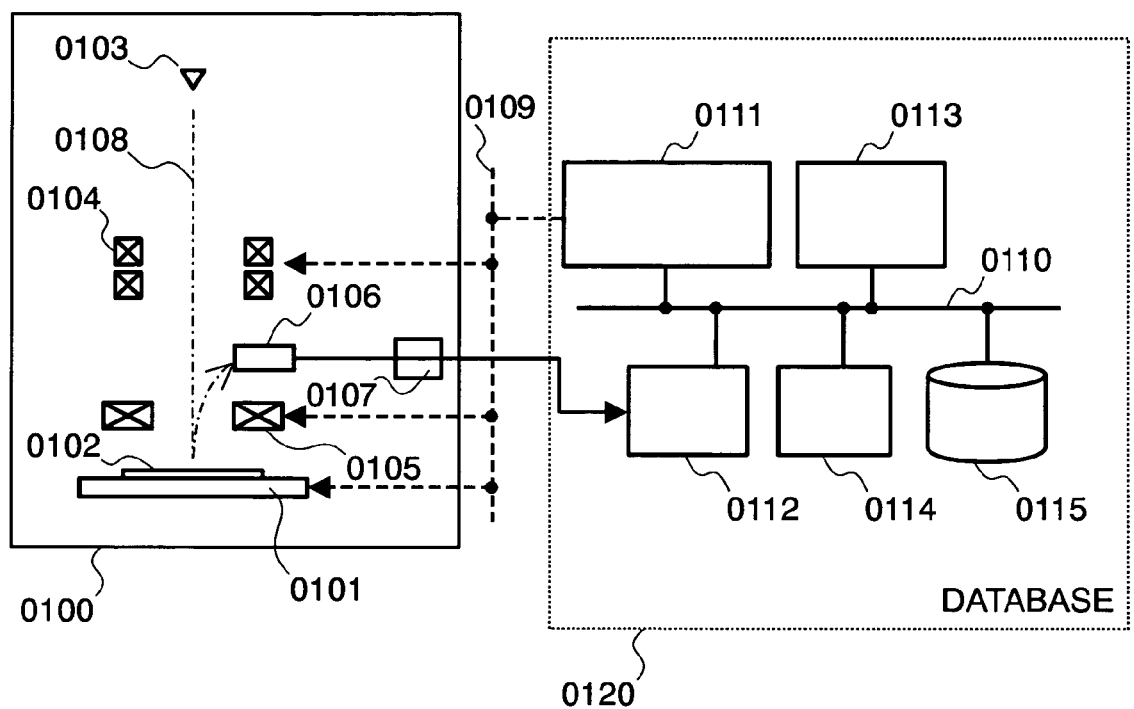
FIG. 1 is a block diagram showing the structure of a scanning electron microscope according to an embodiment of the present invention.

FIG. 1 shows the structure of a scanning electron microscope apparatus according to the present invention. This apparatus is divided broadly into two parts, which consist of an electron optics system 0100 for obtaining electron beam images and an information processing system 0120 for measuring an object pattern by processing the electron beam images. The electron optics system 0100 mainly includes a stage 0101 on which a sample 0102 is mounted, an emission source 0103 which emits an electron beam 0108, a deflector lens 0104 which deflects the electron beam 0108, an objective lens 0105 which is controlled to pick up an image at the in-focus position, a secondary electron detector 0106 which has the function of converting the secondary electrons coming from the sample into an electric signal, and an A/D converter 0107 which converts the detected electric signal. A digital signal, and a controller 0111, which is provided in the information processing system 0120, controls each of the above-mentioned devices via a control bus 0109. On the other hand, the information processing system 0120 for measuring a picked-up pattern using image data mainly includes a processor 0113 which performs image processing, a memory 0112 which stores image data and various kinds of data used in other processes, an input/output device 0114 which allows a user to input pickup conditions and parameters of image processing and has the function of outputting obtained results, and a database 0115 which is referred to in dimension measurement processing of the present invention. These devices transmit and receive data between themselves via a data bus 0110. Further, the controller 0111 shown in FIG. 1 not only controls the electron optics system 0100, but it also exercises control when the information processing system 0120 measures the dimension of a pattern using a picked-up image.

A scanning electron microscope according to the present invention creates, from the scanning electron microscope image of the obtained pattern to be measured, an image profile (a profile of electrical signal intensity extracted from the scanning electron microscope image), and it measures the pattern by applying an image profile that the apparatus stores beforehand in the database to an image profile of the pattern to be measured. Since the image profile to be used that is stored in the database is associated with the cross-sectional shape of the pattern beforehand, the apparatus can output a dimension measurement value corresponding to a measuring position in the cross-sectional shape.

First, a creation sequence of the database 0115 and the data thereby created will be described below with reference to FIG. 4. Subsequently, a measurement sequence employing the database 0115 will be described with reference to FIG. 2.

Figure 4:
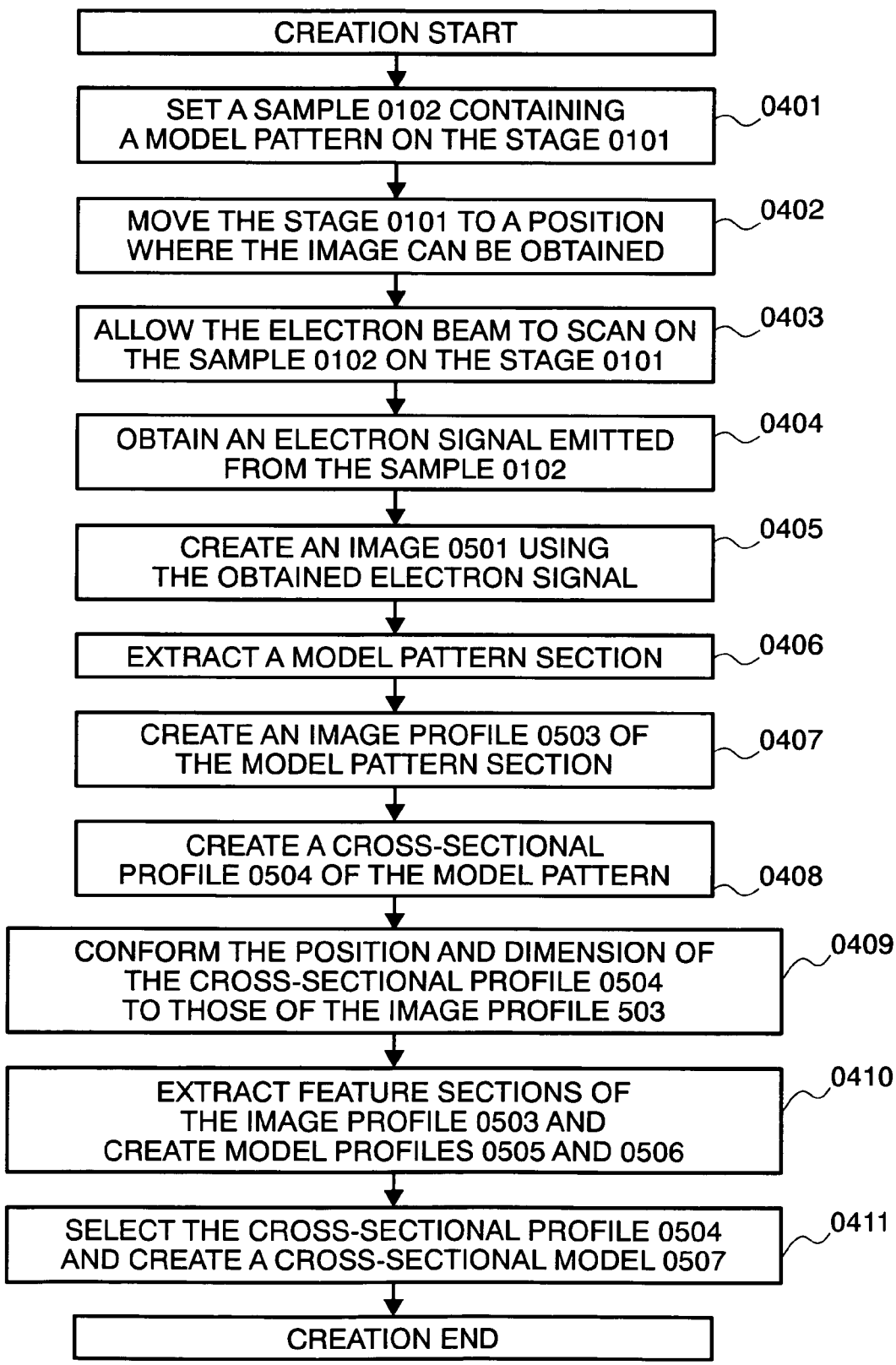
FIG. 4 is a flow diagram showing a process of creating a model profile and a cross-sectional model that are used in pattern dimension measurement.

FIG. 4 is a diagram showing the sequence employed for creation of the database 0115. According to this process, image profiles (an image profile is hereinafter referred to as a model profile) are created corresponding to different cross-sectional shapes that one or more patterns have and cross-sectional models are created corresponding to model profiles by the following process, and these profiles and models are stored in the database 0115. The following is a description of the process of creation of a model profile and of a cross-sectional model corresponding to the model profile, in which a wiring pattern that extends in one direction is used as a model pattern.

In steps described below, a scanning electron microscope image including an image of a model pattern section is obtained. First, a sample 0102 containing a model pattern is set on the stage 0101. (step 0401). Next, the controller 0111 instructs the stage 0101 to move to a position where the image of the model pattern can be obtained by irradiating an electron beam thereon (step 0402). Next, the electron gun 0103 emits the electron beam 0108 and the primary electron beam deflector 0104 deflects the electron beam 0108, thereby allowing the electron beam to scan on the sample 0102 mounted on the stage 0101 (step 0403). At this time, the objective lens 0105 is controlled to pick up the image at the in-focus position.

Next, the secondary electron detector 0106 detects a secondary electron signal from electrons emitted from the sample 0102 by electron beam scanning (step 0404). At this time, a setting value of the objective lens 0105 (a control value of the objective lens at the time of actually picking up the image) is read from the controller 0111, and the magnification for picking up the image is stored in the memory 0112. The reason why this value is stored is because the magnification of the obtained image varies delicately with the setting of the objective lens so that it is necessary that the delicate magnification variation is reflected in subsequent dimension calculation processing to calculate collected dimensions.

Figure 5A:
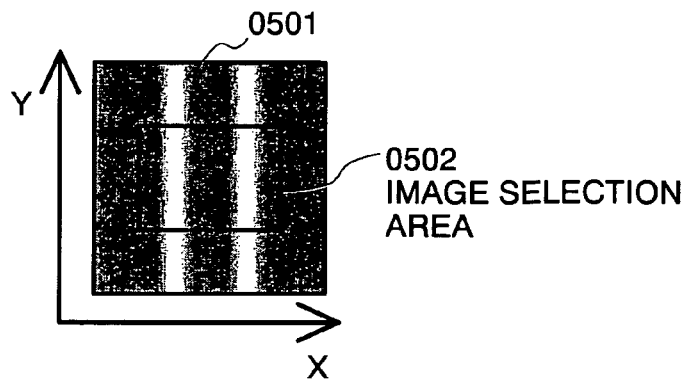
FIG. 5A is a diagram which shows an SEM image.

Next, the A/D converter 0107 converts the obtained secondary electron signal into a digital signal. After preprocessing, such as noise processing is performed on the digitized signal, the resulting data is stored in the memory 0112 in the form of a two-dimensional digital image (step 0405). In the description below, it is to be assumed that the X-axis indicates the width direction in which dimensions are measured and the Y-axis indicates the direction perpendicular to the width, as shown in FIG. 5A. By the processing up to this point, there is obtained a scanning electron microscope image 0501, including the image of the model pattern section as shown in FIG. 5A.

Figure 5B:
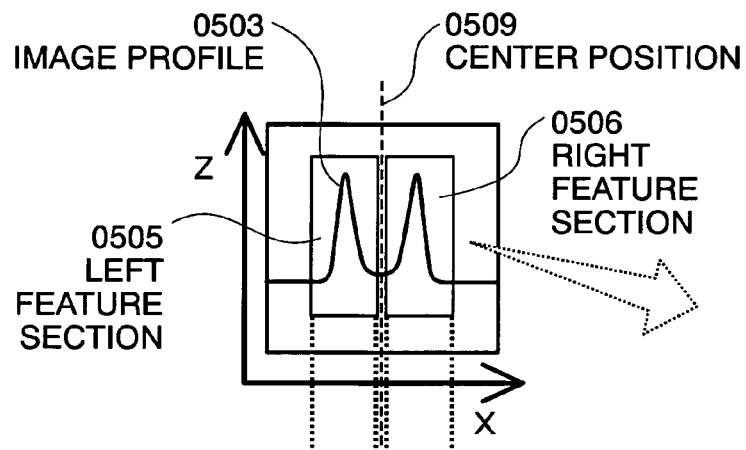
FIG. 5B is a diagram which shows an image profile.

Further, in the steps described below, the model pattern section is extracted from the obtained image 0501 and an image profile thereof is created. First, an image area 0502 (see FIG. 5A) necessary to create the image profile of the model pattern section is selected from the scanning electron microscope image 0501 (step 0406). The necessary image area contains at least the whole model pattern section in the X direction; and it contains, in the Y direction, the necessary number of pixels for the processing in which the pixel values of X are equalized in the Y direction to reduce noise specific to scanning electron microscope images. For example, in the case of measuring the width of the wiring pattern that extends in one direction in the scanning electron microscope image, as shown in this embodiment, there is selected an image area that contains 200 pixels in the Y direction. In this case, the greater the number of pixels used in the equalization of image values, the more the noise specific to scanning electron microscope images can be reduced. Further, a selection area in the Y direction can be changed as necessary in accordance with the shape of a model pattern. Next, in the selected image area 0502, processing is performed in which the pixel values (signal intensity values) of X are equalized in the Y direction, and an image profile 0503 in the X direction is created as shown in FIG. 5B (step 0407). By the processing up to this point, the image profile 0503 of the model pattern section is created.

Figure 5E:
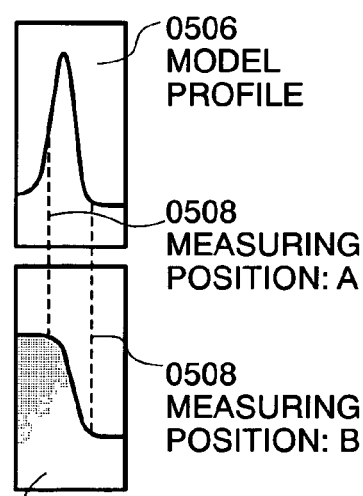
FIG. 5E is a diagram which shows a cross-sectional model and a corresponding model profile.
Figure 5D:
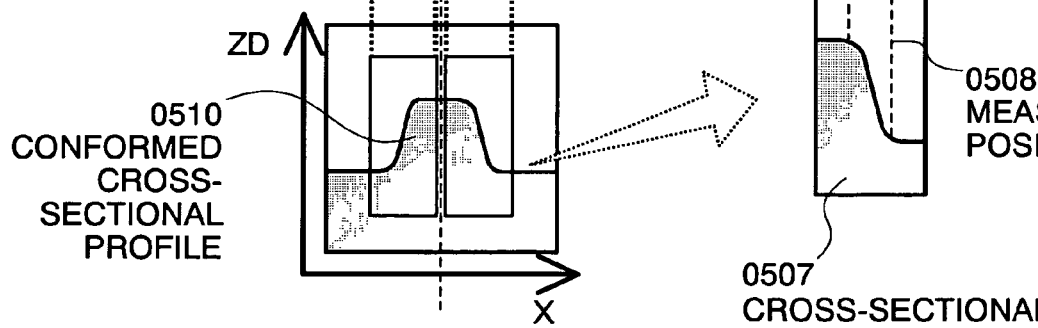
FIG. 5D is a diagram which shows a conformed cross-sectional profile.
Figure 5C:
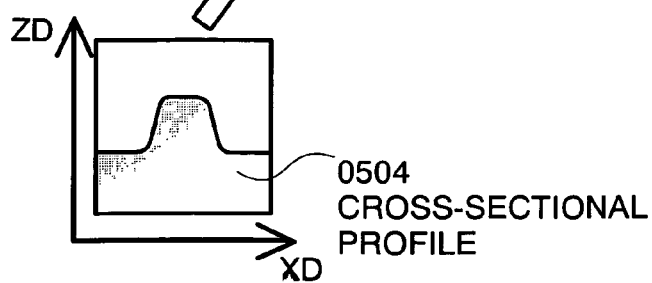
FIG. 5C is a diagram which shows a cross-sectional model.

Next, a cross-sectional profile 0504 of the model pattern is obtained, as shown in FIG. 5C (step 0408). The cross-sectional profile 0504 represents ZD values as heights of the cross section at XD values, where the XD-axis indicates the width direction in which dimensions are measured and the ZD-axis, which is perpendicular to the XD-axis, indicates the height direction of the cross-sectional profile. Methods for obtaining the cross-sectional profile include a method for measuring the model pattern by use of a AFM (Atomic Force Microscope) and a method for observing and measuring the cross section of the model pattern with another microscope, etc. Further, it is also possible to employ, as the cross-sectional profile, a cross section reconstructed using the parallaxes from a plurality of scanning electron microscope images (tilt images) that are picked up, with the electron beams tilted.

Next, the position and dimension of the XD-coordinate of the cross-sectional profile 0504 are thoroughly conformed to the position and dimension of the X-coordinate of the image profile 0503 (step 0409). A specific example of a conforming method will be taken into consideration below. First, the cross-sectional profile 0504 is expanded or contracted such that the X-axis and the XD-axis are identical in dimension. Next, the center position 0509 of the cross-sectional profile 0504 is conformed to the center position 0509 of the image profile 0503. At this time, the center position of the image profile 0503 can be calculated as the middle position between two signal peaks obtained at the side slopes of the cross section. This calculation utilizes the property that a profile obtained by a scanning electron microscope has two large convex shapes in the case of a wiring pattern that extends in one direction.

Lastly, the XD-coordinate of the conformed cross-sectional profile 0504 is replaced with the X-coordinate of the image profile 0503, and a conformed cross-sectional profile 0510 is created as shown in FIG. 5D, thereby representing an image profile value (intensity value) (FIG. 5B) and a cross-sectional profile value (height value of the cross section) (FIG. 5C) that correspond to the same X-coordinate. Thus, by thoroughly conforming the position and dimension of the cross-sectional profile to the position and dimension of the image profile, it is possible to obtain an image profile value corresponding to the position at the steepest slope in the cross-sectional profile 0510, and it is also possible to represent the image profile value of a position, indicated with the ratio of the maximum height of the cross-sectional profile to the minimum height, as the ratio of the maximum height of the image profile to the minimum height. In this manner, an arbitrary point of the cross-sectional profile 0510 can be associated with the corresponding point of the image profile 0503.

As described with respect to this embodiment, in the case of a wiring pattern that extends in one direction, the image profile 0503 obtained by the scanning electron microscope has generally two large convex shapes, as shown in FIG. 5B, and the convex shapes correspond to the respective side slopes of the cross section. The left side of the two convex shapes is extracted as a left feature section 0505 of the image profile, and the right side is extracted as a right feature section 0506 of the image profile. The two sections are designated as model profiles 0505 and 0506, respectively (step 0410). In accordance with the present invention, the image profile 0503 is not employed as the model profile without being processed, but the left and right profiles are separately employed as model profiles 0505 and 0506, respectively. The reason for this is as follows. The left and right model profiles 0505 and 0506 are shifted in the X direction individually for the image profile of a pattern to be measured, and they are applied to the dimension measurement image profile at the coordinate where each model profile matches best with the image profile, thereby making it possible to measure the dimension more accurately with fewer models.

Lastly, there are selected cross-sectional profile sections corresponding to the model profiles 0505 and 0506, respectively, and there is created a cross-sectional model 0507 associated with a model profile (step 0411). In this manner, there are created one or more sets of a dimension measurement image 0601, a model profile 0602, and a cross-sectional model 0603 associated with the profile, which are then stored in the database 0115 (FIG. 6).

Referring now to FIG. 2, a description will be given of a pattern dimension measurement sequence according to the present invention. This sequence is designed to measure the width of a wiring pattern that extends in one direction, and it has the feature of employing a model profile and a cross-sectional model associated with the profile, which are stored in the apparatus.

First, in the same manner as in steps 0401-0405, which have been described with reference to FIG. 4, a scanning electron microscope image 0301, including an image of a pattern section to be measured, is obtained in steps 0201-0205 shown in FIG. 2.

Figure 3A:
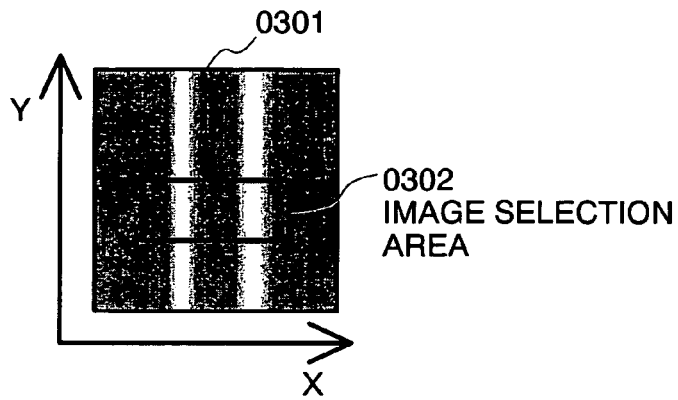
FIG. 3A is a diagram which shows an SEM image.

Next, in the steps described below, a pattern section to be measured is extracted from the obtained image 0301 shown in FIG. 3A, and an image profile is created. First, an image area 0302 necessary to create the image profile of the pattern section to be measured is selected from the scanning electron microscope image 0301 (step 0206). The necessary image area contains, in the X direction, at least the whole pattern section to be measured, and it contains, in the Y direction, the necessary number of pixels for the processing in which the pixel values of X are equalized in the Y direction to reduce noise specific to scanning electron microscope images. For example, in the case of measuring the width of the wiring pattern that extends in one direction in the scanning electron microscope image, as provided in this embodiment, there is selected an image area that contains 200 pixels in the Y direction. In this case, the greater the number of pixels used in the equalization of image values, the more the noise specific to SEM images can be reduced. Further, a selection area in the Y direction can be changed as necessary in accordance with the shape of a pattern to be measured.

Next, in the selected image area 0302, processing is performed in which the pixel values (signal intensity values) of X are equalized in the Y direction, and an image profile 0303 in the X direction is created (step 0207). By the processing up to this point, the image profile 0303 of the pattern section to be measured is created.

Figure 3B:
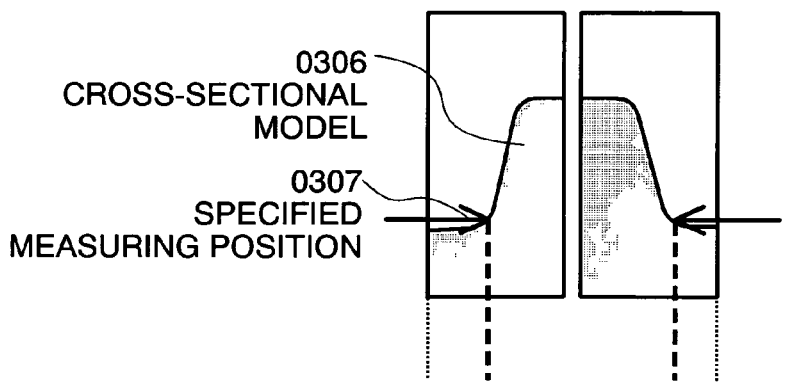
FIG. 3B is a diagram which shows a cross-sectional model.
Figure 3C:
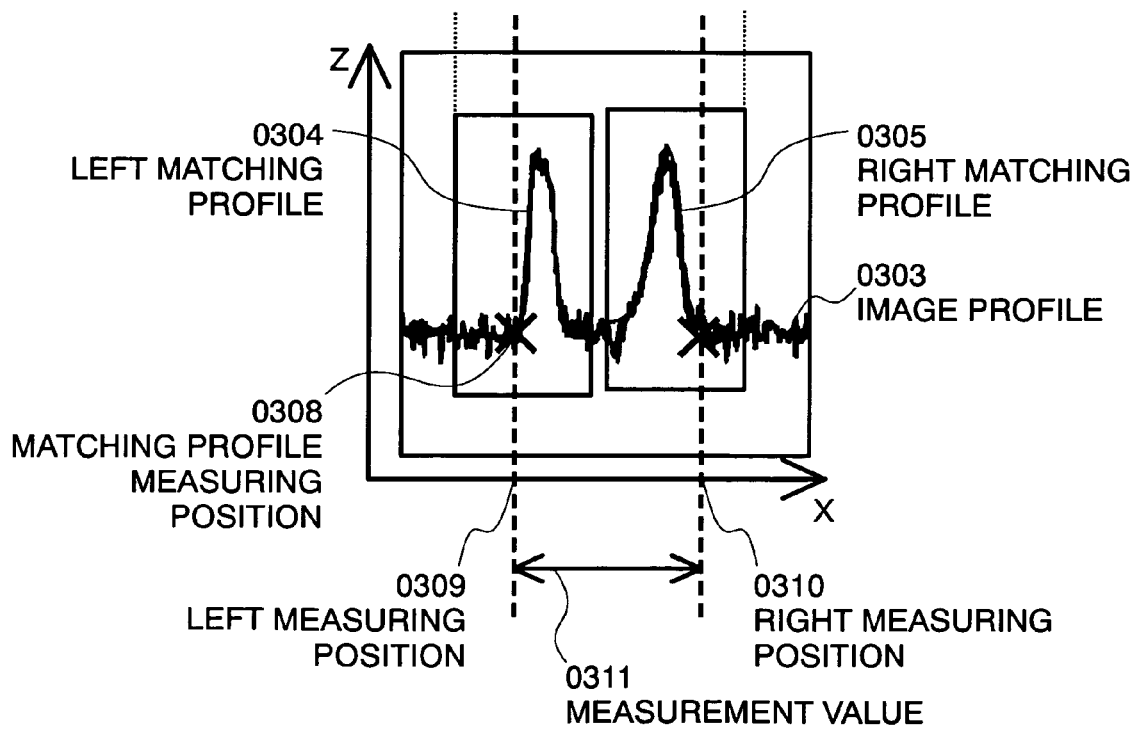
FIG. 3C is a diagram which shows an image profile.

Next, with processing using a fitting method as described below, the model profile that matches best with the created image profile 0303 of the pattern section to be measured is retrieved and applied to the image profile 0303. As described in accordance with this embodiment, in the case of a pattern section to be measured that extends in one direction, the image profile 0303 has two large convex shapes, as shown in FIG. 3C. These two shapes are designated as a left feature section and a right feature section. First, the respective model profiles that match best with the left feature section and the right feature section of the image profile are retrieved from the database 0115 (as shown in FIG. 6) that has been created according to the flow described with reference to FIG. 4. The two sections are designated as a left matching profile 0304 and a right matching profile 0305, respectively, as shown in FIG. 3C (step 0208). At the time of checking the matching rate between each feature section and a model profile, the model profile is shifted in the X direction for the feature section so that the relationship between the amount of shift and the matching rate is checked. The matching rate at the amount of shift by which the model profile matches best with the feature section is designated as the matching rate of this model profile, and the amount of shift at this point is stored.

Respective matching rates, thus obtained, of model profiles in the database being compared, the model profile that matches best with the feature section is designated as a matching profile, and the amount of shift by which the matching profile has matched best with the image profile is stored as the optimal amount of shift. It is possible to employ, as a method of calculating the matching rate, the square error of two profiles (the sum of the square values of the differences between the Z values (values on the Z-axis of FIG. 3C) of two profiles over the whole range of the profiles), for example. In this case, a high matching rate leads to a small value of the square error. Next, the left and right matching profiles 0304 and 0305 are applied to the image profile 0303 in accordance with each amount of shift (step 0209). By the processing up to this point, the model profiles that match best with the created image profile can be retrieved and applied to the image profile 0303.

Next, in the steps to be described below, a measuring position is specified. In order to measure the width of the wiring pattern accurately, it is necessary to specify a measuring position in a pattern cross section corresponding to the matching profile and to substitute a measuring position in the matching profile for it. Therefore, a cross-sectional model 0306, as shown in FIG. 3B, corresponding to the left matching profile 0304 shown in FIG. 3C, is retrieved from the database 0115, and a measuring position 0307 on the cross-sectional model 0306 is specified (step 0210). Next, a measuring position 0308 on the matching profile corresponding to the specified measuring position 0307 on the cross-sectional model is selected, and a X-coordinate 0309 of the selected measuring point on the image profile is stored (step 0211). Steps 0210 to 0211 are performed on the right matching profile as well.

In the case of specifying a measuring position with a plurality of cross-sectional models, as described in this embodiment, it is possible to specify one height or different heights for each cross-sectional model. Further, it is possible to specify the height with absolute values or height ratios, or to specify the position by angle condition, etc. Furthermore, at step 0211, besides substituting a measuring position on the matching profile for a measuring position on the cross-sectional model, for example, a ratio is calculated between the maximum width and the minimum width in the model profile associated with the cross-sectional model, which ratio corresponds to a measuring point specified in the cross-sectional model, and a position having a brightness value (on the image profile) corresponding to the ratio can be selected as a measuring position.

In the case of successively measuring dimensions of patterns that are so formed as to have primarily the same shape on the sample 0102, it is also possible to first store a measuring position 0307 specified on a cross-sectional model 0306 and to successively specify measuring positions 0307 on cross-sectional models 0306 using the stored data at step 0210.

By checking the width 0311 between the measuring point 0309 of the left matching profile and the measuring point 0310 of the right matching profile and converting the pixel coordinates into a dimension based on conditions, such as the magnification (stored in the memory 0112) for picking up the SEM image, the width of the wiring pattern can be calculated (step 0212).

Thus, it is possible to measure the width of the wiring pattern using the database 0115 storing model profiles and cross-sectional models associated with the model profiles.

Up to this point, a series of steps according to the present invention has been described; however, other alternatives may be employed in each step.

For example, at step 0203 of the measurement sequence shown in FIG. 2, when the electron beam 0108 scans on the sample 0102 that is mounted on the stage 0101, the irradiation angle of the electron beam or the stage 0101 may be tilted. For example, by picking up an image with the stage or the incident angle of the beam tilted at a 5-degree angle, an image similar to the pattern observed from diagonally above with a tilt of 5 degrees can be obtained. Consequently, there is an advantage in that observing the bottom of the cross section or the wall of the pattern to be measured becomes easier compared to the case with no tilt of the stage or the electron beam. In accordance with the invention, in the case of thus tilting the stage or the electron beam, it is necessary to employ a model created on the same electron-beam-scan condition at step 0403 in FIG. 4.

Further, at step 0204 in FIG. 2, the secondary electron signal to be obtained may be replaced with a signal obtained by detecting reflection electrons. In this case, at the time of measuring the dimension with the thereby obtained image, there is used a model created by obtaining a reflection electron signal, at step 0404 in FIG. 4.

Further, at step 0206 in FIG. 2 and step 0406 in FIG. 4, it is also possible to select a plurality of dimension measurement pattern sections from one scanning electron microscope image. In the case where, as described, there are a plurality of dimension measurement patterns in the obtained image, steps 0207 to 0212 and steps 0407 to 0411 are performed on each model pattern.

Further, the heights of a plurality of model profiles (e.g., 0506) created by performing the sequence in FIG. 4 may be normalized values. In this case, at the time of retrieving the model profile that matches best with the image profile 0303 at step 0208, with the model profile being expanded or contracted in the height direction, the matching rate at the height where the model profile matches best with the image profile is designated as the matching rate of the model profile. At the time of applying the matching profile to the image profile at step 0209, there is used a model expanded or contracted to the height where the model profile matches best with the image profile.

Further, in the above description, in steps 0401 to 0407 in FIG. 4, the model profile is created from the image profile obtained from the scanning electron microscope image of the model pattern, and the cross-sectional model is created from the cross-sectional profile of the model pattern measured by AFM, etc. However, the image profile and the cross-sectional model may be created using electron beam simulation instead of the above-mentioned processing. In this case, by first creating a cross-sectional model and performing the simulation of irradiating an electron beam on the cross-sectional model, an image profile corresponding to the cross-sectional model can be obtained.

Further, at step 0208 in FIG. 2, in the case where the matching rate of the model profile that matches best with the image profile 0303 falls below a predetermined value, the apparatus can notify a user that an appropriate model profile does not exist. In this case, if an AFM-equipped scanning electron microscope (not shown) is employed, it is possible to obtain a cross-sectional shape by measuring a pattern with the AFM and to store in the database 0115 a new model created by combining the cross-sectional shape with the image profile 0303.

Further, at step 0210 in FIG. 2, at the time of specifying the measuring position on the cross-sectional model 0306 shown in FIG. 3B, a feature point on the cross-sectional model may be specified as a measuring position by specifying a name 0508 after giving the name 0508, to the feature point on a cross-sectional model 0507 (see FIG. 5E) and storing it. For example, the user specifies a part that the user usually wants to measure, such as the bottom of the wiring pattern, in the cross-sectional model 0507, and gives a character string "bottom" or the like that can be easily interpreted by the user to the part as its name. Consequently, by specifying the name of "bottom" at the time of specifying the measuring position, the dimension of the bottom of each wiring pattern can be measured.

Further, by specifying the measuring positions on the matching profiles 0304 and 0305 that have been applied to the image profile 0303 shown in FIG. 3C instead of specifying the measuring position on the cross-sectional model 0306 shown in FIG. 3B at step 0210 in FIG. 2, the dimension measurement may be performed at step 0212. In the method of specifying a measuring position on a matching profile, it is possible to specify a height on the profile with an absolute value or a height ratio, or to specify a position by an angle, etc., as well as specifying an arbitrary point.

FIG. 9 shows an example of an output screen representing a dimension measurement result in the scanning electron microscope according to the present invention. In this screen, there is provided a function of providing measurement results to the user by displaying, on the same screen, various information, such as a picked-up image of a dimension measurement pattern, a dimension obtained therefrom, and a model profile for use in calculating the dimension. In the figure, the scanning electron microscope image 0902 represents the image of a pattern to be measured, and the image profile 0903 extracted from the image 0902 is overlaid on the image 0902.

Further, a matching profile 0904 represents the selected model profile that has matched with the image profile 0903 and is also overlaid on the same screen.

Thus, by overlaying the profile retrieved with matching on the profile extracted from the obtained image, it is possible to visually check the matching rate of the matching profile to the image profile of the pattern to be measured. Further, at this time, a matching rate 0905 may be displayed as well. FIG. 9 also shows an example in which a measuring point 0906 on the matching profile, a cross-sectional model 0907 corresponding to the matching profile, and a measuring point 0908 on the cross-sectional model are displayed together. Thus, by outputting the information on the same screen, it is possible for the user to obtain measuring points visually.

Further, FIG. 9 also shows an example of displaying the name 0508 written along with a dimension 0901 of the measured pattern in the case where the user has specified a position on the cross-sectional shape to be measured with a name, such as "bottom". Displaying such information enables the user to check dimension measurement results easily.

Embodiment 2

This embodiment is directed to facilitation of the process of creating the database 0115 shown in FIG. 4. In this embodiment, a dimension measurement is performed with a model profile and a cross-sectional model (which are stored in the database) created using a shape that varies in stages, such as a pattern on an FEM (Focus Expose Matrix) wafer created by changing the exposure value and focus in stages in accordance with a position on the wafer. By employing a model profile and a cross-sectional model whose shapes are predicted to vary in stages makes it possible, instead of obtaining the dimension of a pattern under measurement by determining one model profile that matches with the image profile of the pattern, to obtain the dimension of the pattern under measurement by interpolation processing using one or more selected cross-sectional models and model profiles that match relatively well with the image profile and resemble it in shape. Therefore, even in the case of a small number of model profiles and cross-sectional models, the dimension measurement can be performed with high accuracy, thereby making it possible to save cost and time for creating models.

Figure 7:
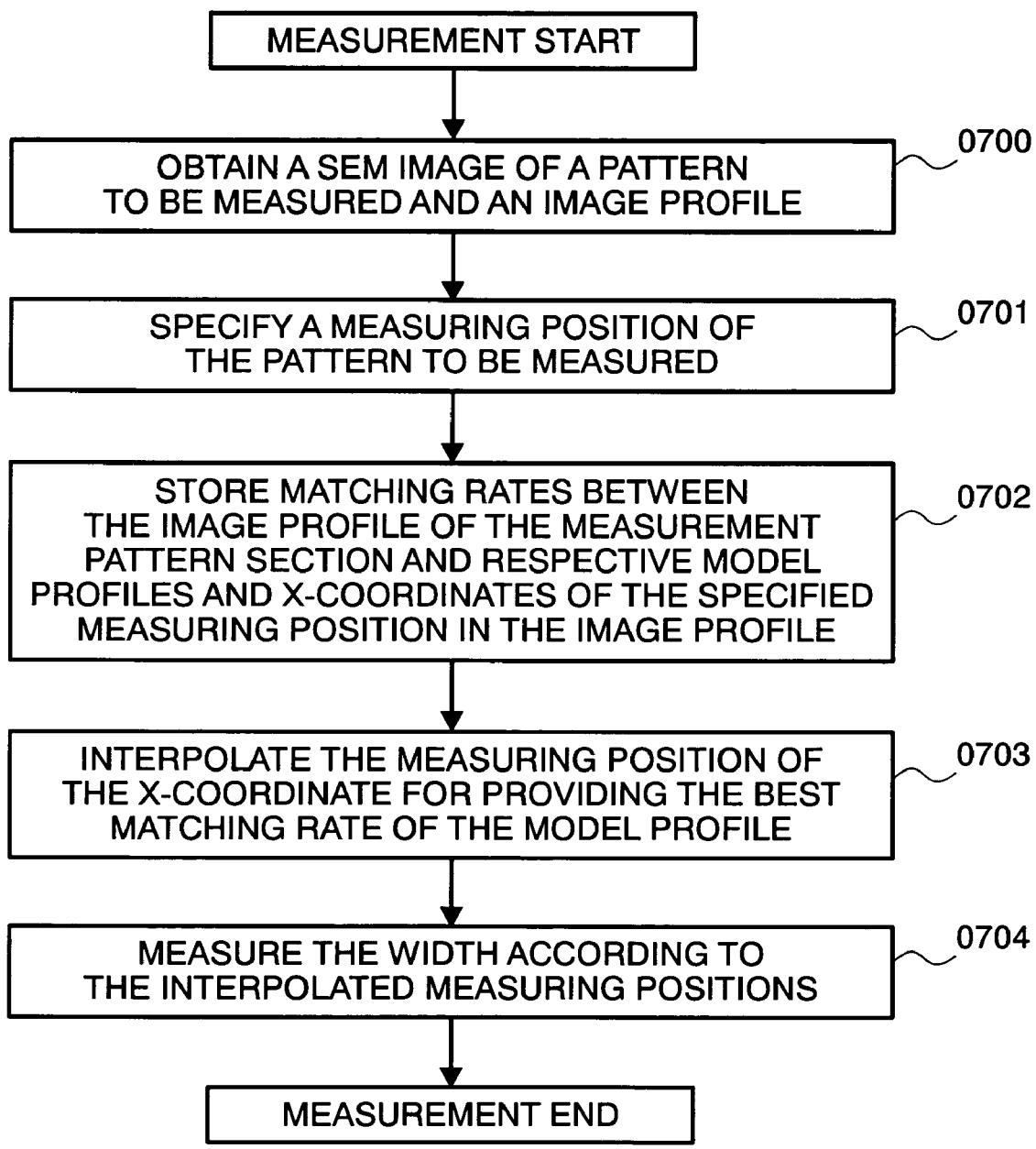
FIG. 7 is a flow diagram showing a pattern dimension measuring process that copes with a small number of models stored in a database.

FIG. 7 shows a pattern dimension measurement sequence according to the present invention. In this measurement sequence, after a scanning electron microscope image of a dimension measurement pattern is obtained and an image profile is obtained from the scanning electron microscope image (step 0700), a measurement is performed using the image profile. However, since step 0700 constitutes the same processing as steps 0201 to 0207 in FIG. 2, the details thereof are omitted in FIG. 7.

Figure 8A:
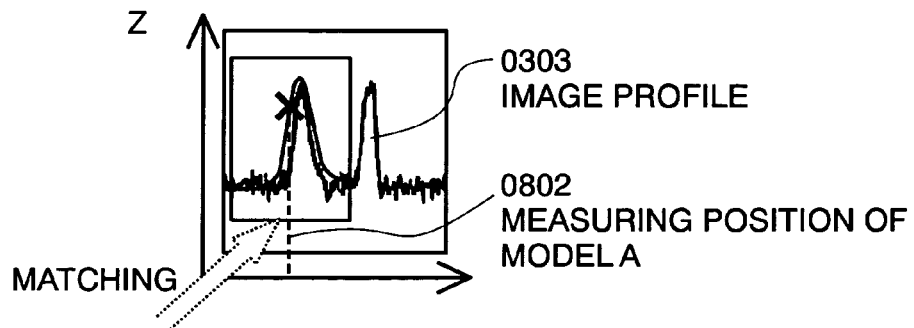
FIG. 8A is a diagram which shows an image profile.
Figure 8B:
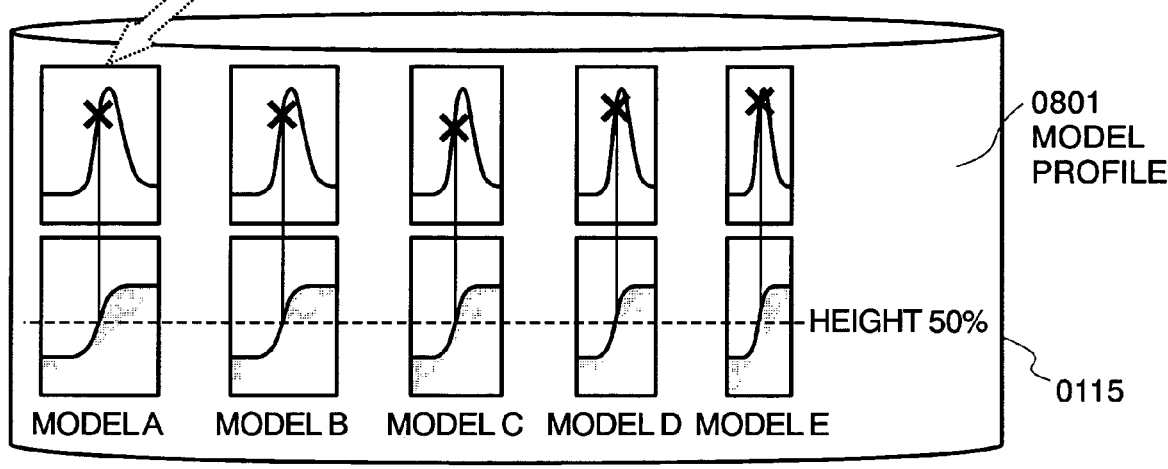
FIG. 8B is a diagram which shows a model profile.
Figure 8C:
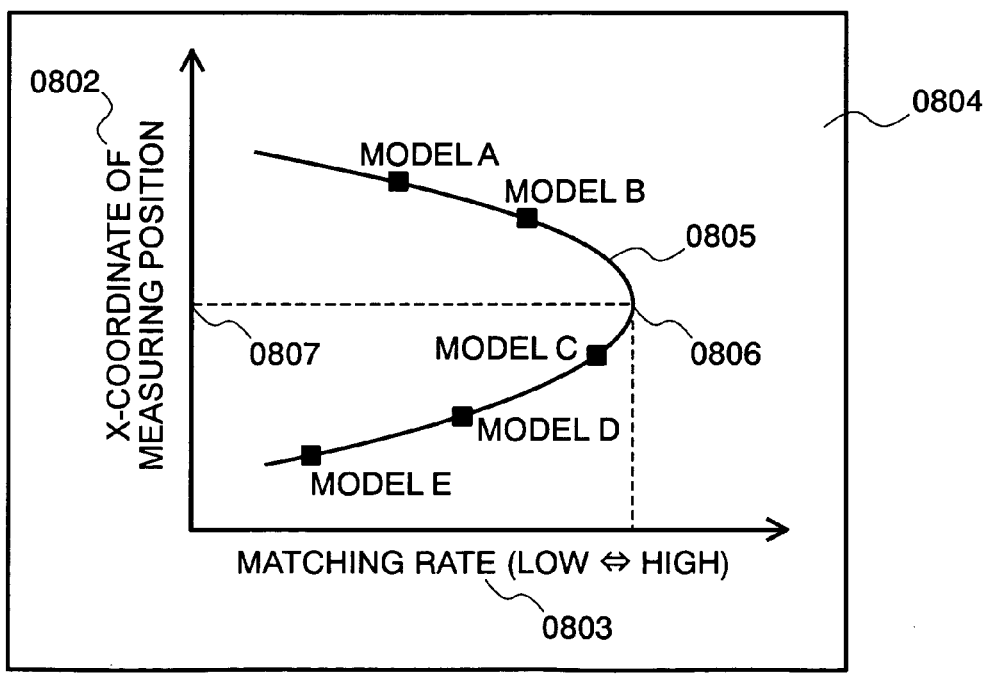
FIG. 8C is a graphical diagram showing a relationship between a matching rate between an image profile and a model profile and a measuring position.

First, a measuring position is specified (step 0701). In this embodiment, a position at 50% of the pattern cross-sectional height is specified. Other specifying methods can include specifying a height with an absolute value or a height ratio and specifying a position by an angle, etc., as well as specifying an arbitrary point on the cross-sectional model. Next, a matching rate 0803 between the image profile 0303 of the pattern to be measured and each model profile 0801 used in this process, as shown in FIG. 8B, is stored, and a X-coordinate 0802 of a specified measuring position in the image profile 0303 is stored (step 0702).

From a relationship 0804 between the matching rate and the X-coordinate of the measuring position thus obtained, a higher matching rate 0806 and its X-coordinate 0807, estimated by a function approximation 0805, etc., are obtained, thereby interpolating the measuring position (step 0703). For example, in the case where the obtained matching rate varies in a rightward convex shape, it can be considered that the matching rate at the peak is higher than the respective matching rates of the model profiles. Therefore, it is possible to perform a dimension measurement by approximating the convex shape with a convex function, such as a parabola, and obtaining the peak and the X-coordinate thereof.

Lastly, the width between the measuring positions obtained at step 0703 is measured, and the pattern dimension is obtained by converting the pixel coordinate into the dimension based on the pickup conditions of the scanning electron microscope image (step 0704).

The first and second embodiments have been directed to a processing for use in the case of measuring a dimension of a pattern that extends in one direction. However, the shape of the pattern to be measured is not limited thereto. Wiring patterns with other shapes, such as circular or elliptical hole patterns, etc., may be measured as well.

The invention may be embodied in other specific forms without departing from the sprit or essential characteristics thereof. Therefore, all embodiments described herein are to be considered in all respects as illustrative and not independent, the scope of the invention being indicated by the appended claims rather than by the foregoing description; and, all changes which come within the meaning and range of equivalency of the claims are therefore intended to be embraced therein.

What is claimed is:

1. A method for measuring a dimension of a pattern, comprising the steps of:
    obtaining a secondary electron image of a sample by picking up an image of the sample using a scanning electron microscope;
    creating an image profile of a pattern whose dimension is to be measured within the obtained secondary electron image;
    retrieving a model profile that matches best with the created image profile from a plurality of model profiles stored in a memory that are obtained respectively from secondary electron images of a plurality of patterns different in shape and in which each of shapes and dimensions of cross sections of the plurality of patterns are known; and
    estimating a cross-sectional shape of the pattern from information of the retrieved model profiles, and obtaining a dimension of the pattern using information of the estimated cross-sectional shape of the pattern.

2. A method for measuring a dimension of a pattern according to claim 1, further comprising the step of displaying the obtained dimension of the pattern, the secondary electron image of the pattern, the image profile, and the model profile, on a screen.

3. A method for measuring a dimension of a pattern according to claim 1, wherein the step of obtaining a dimension of the pattern includes obtaining a dimension of the pattern from the model profile corresponding to a location specified on a cross-sectional profile of the pattern whose cross-section corresponding to the retrieved model profile is of a known shape and dimension.

4. A method for measuring a dimension of a pattern, comprising the steps of:
    creating an image profile of a pattern whose dimension is to be measured from a secondary electron image of a sample, the secondary electron image being obtained by picking up an image of the sample using a scanning electron microscope;

obtaining a model profile that matches best with the image profile from a database that stores a plurality of model profiles that are obtained respectively from secondary electron images of cross sections of a plurality of patterns, the cross sections being of known dimensions and being different in shape;

specifying a location for dimension measurement on a cross-sectional profile of the pattern whose cross-section corresponding to the obtained model profile is of a known dimension;

estimating a cross-sectional shape of the pattern from information of the obtained model profiles;

obtaining a dimension of a desired location of the pattern by using information of the estimated cross-sectional shape of the pattern; and displaying the obtained dimension of the desired location, the obtained model profile, the image profile, and the secondary electron image of the pattern, on a same screen.

5. A method for measuring a dimension of a pattern according to claim 4, wherein the step of specifying a location includes specifying a plurality of locations for dimension measurement, on a cross-sectional profile of the pattern whose cross-section is of a known dimension, and the step of obtaining a dimension includes obtaining dimensions of a plurality of locations of the pattern from locations on the model profile which respectively correspond to a plurality of locations for dimension measurement specified on the cross-sectional profile.

6. A method for measuring a dimension of a pattern according to claim 4, wherein the step of obtaining a model profile that matches best with the image profile from a database includes obtaining a model profile that matches best with the image profile by fitting, as to left and right sides of the pattern.

7. An apparatus for measuring a dimension of a pattern, comprising:

scanning electron microscope means for obtaining a secondary electron image of a sample by irradiating an electron beam converged on a specimen formed on the sample and allowing the electron beam to scan using a secondary electron image obtained by picking up an image of the sample using a scanning electron microscope;

image profile creation means for creating an image profile of a pattern whose dimension is to be measured within the secondary electron image obtained by the scanning electron microscope means using the secondary electron image;

storage means for storing a plurality of model profiles that are obtained respectively from secondary electron images of a plurality of patterns which are different in shape, and in which each of shapes and dimensions of cross sections of the plurality of patterns are known;

model profile retrieving means for retrieving a model profile that matches best with the image profile created by the image profile creation means from the plurality of model profiles stored in the storage means;

cross-sectional shape estimating means for estimating a cross-sectional shape of the pattern from information of the retrieved model profiles; and dimension calculation means for obtaining a dimension of the pattern using information of the estimated cross-sectional shape of the pattern.

8. An apparatus for measuring a dimension of a pattern according to claim 7, further comprising display means having a screen for displaying on the screen thereof, the secondary electron image of the pattern obtained by the scanning electron microscope means, the image profile created by the image profile creation means, the model profile retrieved by the model profile retrieving means, along with the dimension of the pattern calculated by the dimension calculation means.

9. An apparatus for measuring a dimension of a pattern according to claim 7, wherein the dimension calculation means includes a measuring location specifying unit for specifying a location for dimension measurement on a cross-sectional profile, stored in the storage means, of the pattern whose cross-section is of a known dimension; a measuring location determining unit for determining a location, on the model profile retrieved by the model profile retrieving means, which corresponds to the location for dimension measurement specified on the cross-sectional profile at the measuring location specifying unit; and a pattern dimension calculation unit for obtaining a dimension of the pattern from a measuring location on the model profile determined at the measuring location determining unit.

10. An apparatus for measuring a dimension of a pattern according to claim 7, wherein the model profile retrieving means obtains a model profile that matches best with the image profile by fitting, as to left and right sides of the pattern.

\* \* \* \* \*